(12) United States Patent
Schulte-Elte et al.

(10) Patent No.: US 6,235,926 B1
(45) Date of Patent: May 22, 2001

(54) PERFUMING INGREDIENTS OF WOODY, FRUITY ODOR

(75) Inventors: Karl-Heinrich Schulte-Elte, Onex; Hervé Pamingle, Versoix; Christian Vial, Geneve, all of (CH)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 09/397,993

(22) Filed: Sep. 16, 1999

Related U.S. Application Data

(62) Division of application No. 09/085,594, filed on May 28, 1998, now Pat. No. 6,008,186.

(30) Foreign Application Priority Data

Jun. 6, 1997 (CH) .................................................. 1373/97

(51) Int. Cl.$^7$ ........................... C07C 61/29; C07C 35/23; C07C 43/188
(52) U.S. Cl. ........................... 560/256; 568/665; 568/820
(58) Field of Search .................................. 568/665, 820, 568/821, 822; 560/256; 512/15

(56) References Cited

U.S. PATENT DOCUMENTS

| | | | |
|---|---|---|---|
| 2,803,662 | 8/1957 | Stoll | 260/611 |
| 3,929,676 | 12/1975 | Chappell et al. | 252/522 |
| 3,965,189 | 6/1976 | Schulte-Elte et al. | 260/586 |
| 3,966,819 | 6/1976 | Schulte-Elte et al. | 260/586 F |
| 4,218,347 | 8/1980 | Naf et al. | 252/522 R |
| 4,288,349 | 9/1981 | Boelens et al. | 252/522 R |
| 4,302,363 | 11/1981 | Bruns et al. | 252/522 R |

OTHER PUBLICATIONS

M. Colombo et al., "Manganese (III) Acetate and Lewis Acid Mediated Cyclization of Olefinicβ–Keto Esters: A Comparative Study", *Tetrahedron* 46 :4149–4154 (1990).

J. White et al., "Synthesis of Dihydropallescensin D Via Manganesee (III) Mediated Cyclization of an Olefinicβ–Keto Ester", *Tetrahedron Letters* 31 :59–62 (1990).

*Primary Examiner*—Rosalynd Keys
(74) *Attorney, Agent, or Firm*—Pennie & Edmonds LLP

(57) ABSTRACT

The present invention relates to perfumery of compounds of the general formula

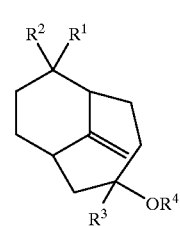

(II)

in which
$R^1$ and $R^2$ are identical or different and represent each a methyl or ethyl group,
$R^3$ represents hydrogen or an alkyl group from $C_1$ to $C_4$, linear or branched, and
$R^4$ represents hydrogen, an alkyl group from $C_1$ to $C_4$, linear or branched, or an acyl group of formula $R^5C(O)$—, $R^5$ being hydrogen or an alkyl group from $C_1$ to $C_4$, linear or branched.

The novel odoriferous character of these compounds is the combination of woody with fruity notes.

3 Claims, No Drawings

PERFUMING INGREDIENTS OF WOODY, FRUITY ODOR

CROSS REFERENCE TO RELATED APPLICATIONS

This application is a division of prior application Ser. No. 09/085,594 filed on May 28, 1998, now U.S. Pat. No. 6,008,186.

TECHNICAL FIELD AND PRIOR ART

The present invention relates to novel perfuming ingredients. It relates, more particularly, to compounds of the general formula

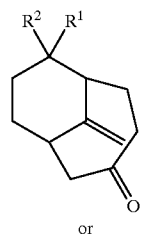

(I)

or

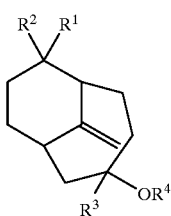

(II)

as defined further on, and their use in perfumery.

The said compounds possess novel odoriferous properties, namely woody and, fruity odors this combination being unknown in the prior art compounds. The application also concerns syntheses and novel intermediate products which serve to prepare said compounds.

The compounds which are the object of the present invention show as a common feature the bicyclic carbon framework 7,7-dimethyl-10-methylene-bicyclo [4.3.1] decane which carries osmophoric groups comprising an oxygen atom in the exocyclic 3-position. The bicycle can, moreover, comprise other substituents, for example alkyl groups.

The use in perfumery of substances of similar structure, which comprise the bicyclic system 6,6-dimethyl-9-methylene-bicyclo[3.3.1]nonane, thus having one carbon atom less in the cycle carrying the osmophoric group, has been known for a long time. From an olfactive point of view, the most important substance of this well-known group is 2-ethoxy-2,6,6-trimethyl-9-methylene-bicyclo[3.3.1] nonane of formula

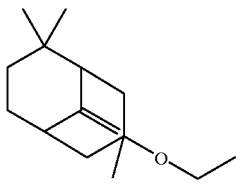

(III)

the synthesis of which was carried out for the first time in the fifties by Stoll et al. (see U.S. Pat. No. 2,803,662). Since then, several syntheses were described for this product, all leading to a mixture of the exo- and endo-ethoxy isomers, with the relative proportions between these 2 isomers varying considerably according to the synthesis which was chosen. A mixture of these isomers is, moreover, sold under the commercial name Physeol (origin: Firmenich SA, Geneva, Switzerland). This commercially available compound has a woody odor which is accompanied by an amber ether note.

We have now discovered that the presence of a supplementary carbon in the cycle carrying the osmophoric group gives rise to odoriferous properties which are clearly distinct from those of Physeol and of its analogues, namely woody and amber notes to which there is added an intense fruity note, in particular of the rhubarb or grapefruit type. In view of the knowledge of the odor properties of bicyclic compounds of the 6,6-dimethyl-9-methylene-bicyclo[3.3.1] nonane type, mentioned above, and of Physeol in particular, this result is thus very unexpected and renders the compounds (I) and (II) particularly useful in perfumery due to the combination of the above-mentioned odor characteristics.

DESCRIPTION OF THE INVENTION

The object of the present invention is thus to provide novel perfuming ingredients showing the above-mentioned specific odor, and the synthesis of said products.

Therefore, the present application describes compounds of the general formula

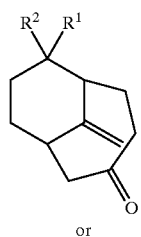

(I)

or

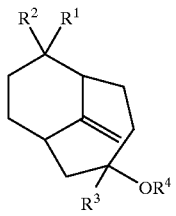

(II)

in which
$R^1$ and $R^2$ are identical or different and represent each a methyl or ethyl group,
$R^3$ represents hydrogen or an alkyl group from $C_1$ to $C_4$, linear or branched, $R^4$ represents hydrogen, an alkyl group from $C_1$ to $C_4$, linear or branched, or an acyl group of formula $R^5C(O)$—, $R^5$ being hydrogen or an alkyl group from $C_1$ to $C_4$, linear or branched, and their use in perfumery.

The common feature of the compounds of the present invention containing the bicycle 7,7-dimethyl-10-methylene-bicyclo[4.3.1]decane oxo-substituted in position 3, is their olfactive character. Their odor can be described as a woody note, together with an intense fruity note. The quality and intensity of said fruity note can be of varied nature, but the woody bottom note is always clearly present, rendering said compounds particularly useful in perfumery.

Of course, in spite of the fact that the compounds of the present invention possess a common odor of the woody-fruity type, there are differences between the various products, and these can be quite pronounced. These differences cannot only reveal themselves between compounds of different chemical structure, but even between stereoisomers of a given compound.

The odoriferous properties of the compounds of the invention are best represented in 7,7-dimethyl-10-methylene-bicyclo[4.3.1]dec-3-yl acetate and in 3-methoxy-7,7-dimethyl-10-methylene-bicyclo[4.3.1]decane. These two compounds are thus preferred according to the invention.

7,7-Dimethyl-10-methylene-bicyclo[4.3.1]dec-3-yl acetate, in the form of a mixture of isomers of the exo and endo configuration, develops a woody note which is accompanied by a note of the rhubarb type. The overall impression of the odor of this compound is that of a woody-rooty note of the Vetyver type, with the rooty character being accompanied by the mentioned fruity character. This olfactive character is very prized in fine perfumery.

The two exo and endo isomers of this compound show distinct odors. The exo isomer, in fact, develops an odor in which the woody, cedar character is more marked, whereas the endo isomer possesses a woody note in which the odor characters of the rhubarb and grapefruit types are very pronounced.

3-Methoxy-7,7-dimethyl-10-methylene-bicyclo[4.3.1]decane also exists in two stereoisomeric forms, namely as exo and endo configuration isomers, which show odoriferous features which are different from each other or even from those of their mixture. The endo isomer develops a citrus-grapefruit odor, reminiscent of nootkatone, which is very strong, whereas the exo isomer shows a warm, typical, woody note with an aspect reminiscent of AMBROX® (8,12-epoxy-13,14,15,16-tetranorlabdane, registered trademark of Firmenich SA, Geneva, Switzerland) and orris. The mixtures of these two isomers possess a voluminous odor wherein the woody and grapefruit notes are very substantive and tenacious. Generally, the two isomers as well as their mixtures, are all useful perfuming ingredients.

The compounds of formulae (I) and (II) can be used just as well in fine perfumery as in functional perfumery, and this in the form of one of their pure isomers or in form of a mixture of these. They have revealed themselves appropriate for the preparation of various perfuming compositions, bases and perfuming concentrates, as well as for perfumes and colognes, to which they confer a woody-fruity character. Their use for the perfuming of various articles, like soaps, bath or shower gels, shampoos, hair-conditioning creams and lotions, cosmetic preparations, body deodorants or air fresheners is also advantageous.

Moreover, they are also appropriate for the perfuming of detergents or fabric softeners and of all-purpose household cleaners.

The proportions in which the compounds of the present invention can be used in the various above-mentioned products varies within a wide range of values. These values depend on the nature of the product to be perfumed and the desired olfactive effect. They also depend on the nature of the coingredients in a given composition, when the compounds of the invention are used in admixture with other perfuming ingredients, solvents or adjuvants of current use in the art. The compounds of the present invention can of course also be added to the perfuming compositions or perfumed articles either as such or in solution in solvents of current use in the art.

As an example, there can be cited concentrations of the order from 1 to 10%, even 20% or more, by weight with respect to the perfuming composition into which they are incorporated. Much lower concentrations than those cited above can be used when the compounds are used for the perfuming of the various products cited above.

The invention also concerns a process for the preparation of a compound of formula

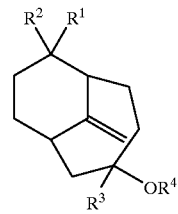

(II)

in which symbols $R^1$ to $R^4$ have the meaning as defined above, wherein said process comprises the following steps:

a) the reaction of a compound of formula

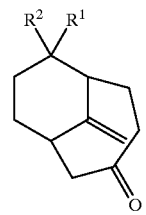

(I)

in which $R^1$ and $R^2$ have the meaning indicated for formula (II), with a reducing agent, to obtain the corresponding compound of formula (II) in which $R^3$ and $R^4$ each represent hydrogen; or b) the reaction of a compound of formula (I) with an appropriate organometallic compound to form the corresponding compound of formula (II) in which $R^3$ represents an alkyl group from $C_1$ to $C_4$, linear or branched, and $R^4$ represents hydrogen;

c) if necessary, the etherification of the compound (II) obtained in step a) or b) to form the corresponding ether;

d) if necessary, the esterification of the compound (II) obtained in step a) or b) to form the corresponding ester.

The key products in the process described are the cyclic ketones (i) from which the desired products are available. These ketones can be prepared as is shown in scheme I. By a chemical modification of the keto function, osmophoric groups of different character can be created, giving rise to variations in the olfactive character of the formed molecules.

The prior art describes an analogous process to that shown in scheme I, for the preparation of the ketone of formula (I) in which $R^1$ and $R^2$ each represent a methyl group (see, for example, A. Ruveda et al., Tetrahedron 1990 (46), 4149; J. D. White, T. C. Somers et K. M. Yager, Tetrahedron Lett. 1990 (31), 59). Said process makes use of α-dihydroionone as starting product, corresponding to formula (IV) of the following scheme I, with $R^1=R^2=$methyl. The odor of the thus-obtained ketone, or 7,7-dimethyl-10-methylene-bicyclo[4.3.1]decan-3-one, which is of the woody type with a note reminiscent of borneol, has never been described in literature. This ketone has therefore also been found to be a useful perfuming ingredient.

The other starting product s which are represented in scheme I and which correspond to formula (IV) are commercially available or can be easily obtained from commercial products.

The following scheme II shows the possibilities for the conversion of the ketones of formula (I).

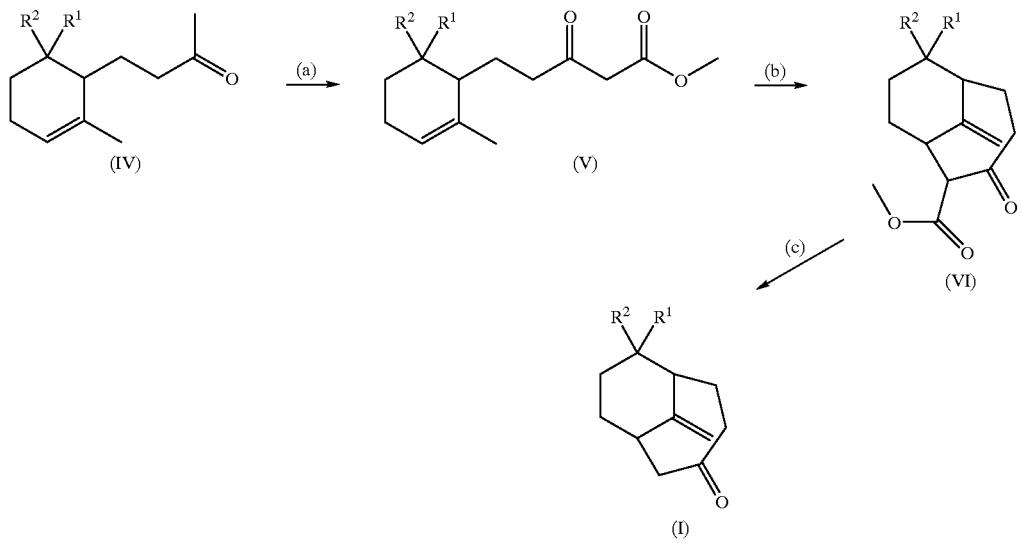

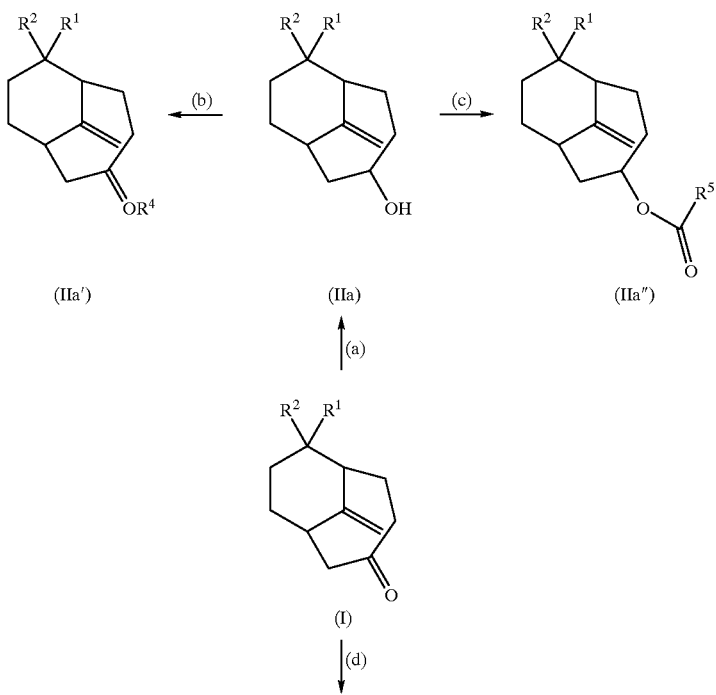

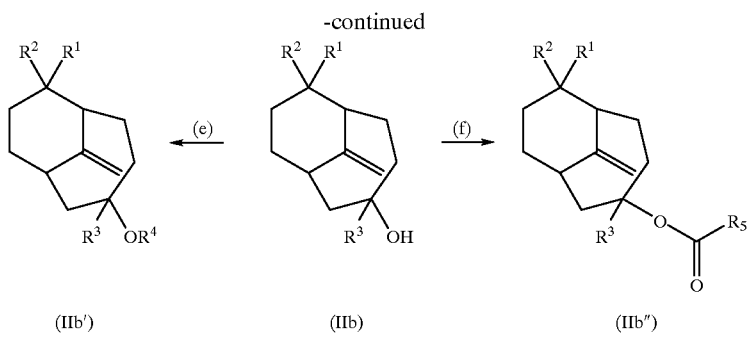

(IIb')  (IIb)  (IIb")

From the above scheme II, it is apparent that the ketones (I) can be directly reduced to give the corresponding alcohols (IIa), by using appropriate reducing agents. In this context, one can cite, for example, LiAlH$_4$ or NaBH$_4$. The solvent in which the reduction is carried out is chosen from ethers, for example, THF or diethyl ether, or alcohols, for example methanol or ethanol. It is evident that, further to the above-cited reducing agents and solvents, there are other agents and solvents which also give satisfying results.

In the same way, the ketones (I) can also react with organometallic reagent (step d) to give, after hydrolysis, the corresponding α-substituted alcohols (IIb). As appropriate metallating agent, one can cite Grignard and organolithium compounds, as well as other metallating agents which are known to a person skilled in the art of this type of reaction. The reaction is carried out in an inert solvent which, if necessary, is capable of stabilizing the organometallic compound. As solvent, there can be used any current solvent for this type of reaction.

The alcohols (IIa) and (IIb) can be transformed into the corresponding ethers (IIa') and (IIb') using etherification agents, for example, steps (b) and (e). An appropriate synthetic way is the Williamson-synthesis which consists in the conversion of an alcohol into an alkali alcoholate and the reaction of the same with the halide of the respective alcane. Alkali hydrides, for example KH or NaH, have been found to be appropriate for the transformation of the alcohol group into an alcoholate. When the alkali salt is formed, the etherification reaction can be carried out with, for example, an alkyl halide. An inert solvent in which the reaction proceeds well is chosen. As examples, one can cite THF or diethyl ether. As the etherification reaction is known in principle, a person skilled in the art is, of course capable of finding other etherification reactions, as well as solvents, which fulfill the requirements of the present invention.

Moreover, the alcohols (IIa) and (IIb) can be esterified, for example, steps (c) or (f), using current reagents, for example the chloride or anhydride of the respective carboxylic acid. The solvents which can be used in the above-mentioned reaction are, like the esterfication reagents, currently known.

The invention will now be described in greater detail in the following examples, in which the temperatures are indicated in degrees centigrade and the abbreviations have the usual meaning in the art.

EMBODIMENTS OF THE INVENTION

EXAMPLES

General remark: all NMR-spectra were recorded in CDCl$_3$.

Example 1
Preparation of Alcohols of Formula (IIb)
General method:

In a 3-necked flask which was equipped with a reflux condenser, a thermometer and a dropping funnel, there were placed, under N$_2$-atmosphere, 2.4 g (0.1 mole) of magnesium turnings. After the addition of 30 ml of anhydrous ether and 1 crystal of iodine, the reaction was started by adding some drops of the appropriate alkyl halide used. Then a solution of 0.12 mole of the appropriate alkyl halide in 50 ml of anhydrous ether was added dropwise, with the solution boiling under reflux. When all magnesium had disappeared, a solution of 0.078 mole of the appropriate ketone of formula (I), namely 7,7-dimethyl-10-methylene-bicyclo [4.3.1]decan-3-one or one of its homologues, in 50 ml of anhydrous ether was added, while letting the reaction take place at reflux. The reaction mixture was subsequently stirred for 2 hours at room temperature, then poured on ice and taken up in ether. The thus-obtained solution was washed with brine and then dried over Na$_2$SO$_4$. After filtration and washing of the residues, the resulting solution was concentrated under vacuo. After chromatographic purification of the product over SiO$_2$, using a mixture of cyclohexane:ether/8:2 as elution agent, the pure product is obtained by distillation in a bulb-to-bulb apparatus, at a pressure of 10 Pa.

a) 3,7,7-trimethyl-10-methylene-bicyclo[4.3.1]decan-3-exo-ol alkyl halide used: methyl iodide 11.2 g of a colorless oil, corresponding to 69% of the theoretical yield and formed exclusively of the exo isomer, were obtained.

Odor: woody-cedar note, with a patchouli character and a slight perspiration note.

IR (neat): 3480, 2940, 1450, 900 cm$^{-1}$ $^1$H-NMR (360 MHz): 0.90 (s, 3H); 0.94 (s, 3H); 1.09 (m, 1H); 1.16 (s, 3H); 1.38 (m, 1H); 1.52–1.89 (m, 9H); 2.07 (t, J=7 Hz, 1H); 2.51 (m, 1H); 4.76 (d, J=3 Hz, 1H); 4.95 (d, J=3 Hz, 1H) δppm $^{13}$C-NMR (90 MHz): 25.6 (q); 28.12 (q); 28.19 (q); 29.4 (t); 30.1 (t); 32.9 (q); 34.9 (s); 38.2 (d); 40.2 (t); 43 (t); 53.2 (d); 73.5 (s); 111.5 (t); 154.9 (s) δppm MS m/z 208 (M$^+$, 4); 190 (12); 175 (30); 161 (19); 147 (30); 134 (57); 119 (77); 105 (97); 93 (97); 79 (91); 69 (55); 55 (50); 41 (100).

b) 3-ethyl-7,7-dimethyl-10-methylene-bicyclo[4.3.1]-3-decan-ol alkyl halide used: ethyl bromide 12.8 g of colorless oil which was formed of the 2 endo/exo isomers (1/9) in 74% of the theoretical yield were obtained.

Odor: woody-cedar note having an amber character, the perspiration note being less pronounced than in the preceding example.

IR (neat): 3450, 2950, 1660, 1450, 900 cm$^{-1}$ $^1$H-NMR (360 MHz): 0.86–0.93 (m, 9H); 1.08 (m, 1H); 1.41 (m, 3H); 1.47–1.79 (m, 8H); 1.87 (m, 1H); 2.05 (m, 1H); 2.7 (m, 1H); 4.74 (d, J=3 Hz); 4.95 (d, J=3 Hz) δppm MS m/z 222 (M$^+$, 3); 204 (13); 193 (32); 175 (45); 148 (48); 133 (48); 123 (98); 107 (100); 93 (90); 85 (28); 79 (90); 69 (45); 57 (93); 41 (72).

Example 2
Preparation of Ethers of Formula (IIa')
General Method:

In a 3-necked flask which was equipped with a reflux condenser, a thermometer and a dropping funnel, there were placed, under $N_2$-atmosphere, 12 ml (0.06 mole) of a suspension of KH in oil (20%, FLUKA). The hydride is washed three times with anhydrous pentane in order to remove as much oil as possible. Then a solution of 0.049 mole of the respective alcohol of formula (IIb), namely 7,7-dimethyl-10-methylene-bicyclo[4.3.1]decan-3-ol or one of its homologues, in 48 ml of anhydrous THF was added dropwise. The reaction mixture was subsequently stirred for 2 hours before 0.81 mole of the chosen alkyl halide were added dropwise. The reaction mixture was stirred for another 3 hours at room temperature, then poured on ice, taken up in ether and washed with brine to neutrality. After drying over $Na_2SO_4$, the solution was filtered and concentrated in vacuo.

a) 3-methoxy-7,7-dimethyl-10-methylene-bicyclo[4.3.1]decane alkyl halide used: methyl iodide
mixture composed of 2 isomers (29/71).
endo methyl ether (peak 1; 29% of the mixture)
exo methyl ether (peak 2 ; 71% of the mixture)
After distillation over a Vigreux type column, 9.05 g of a colorless oil were obtained.
Yield=88% of theoretical yield.

IR (neat): 3080, 2920, 2800, 1640, 1450, 1100, 880 cm$^{-1}$
$^1$H-NMR (360 MHz): 0.85 (s, 3H exo); 0.87 (s, 3H, endo); 0.91 (s, 3H, exo); 0.92 (s, 3H, endo); 1.05 (m, 1H); 1.35–2.04 (m, 10H);2.09 (dd, J=3, 10 Hz, 1H); 2.53 (m, 1H endo); 2.61 (m, 1H, exo); 3.27 (s, 3H, endo); 3.31 (s, 3H, exo); 4.6 (d, J=3 Hz, 1H, endo); 4.61 (d, J=3 Hz, exo); 4.71 (d, J=3 Hz, endo); 4.83 (d, J=3 Hz, exo) δppm $^{13}$C-NMR (90 MHz): 24.2 (t); 26 (t); 27.3 (q); 28.2 (q); 28.3 (t); 31 (t); 31.2 (t); 34.3 (t); 34.5 (s); 37.3 (d); 41.2 (t); 51.5 (d); 52.6 (d); 55.9 (q); 78.4 (d); 82.3 (d); 110.5 (t); 112 (t); 151.4 (s); 153 (s) δppm The endo- and exo-isomers were prepared in a pure state from the endo- and exo-isomer of 7,7,-dimethyl-10-methylene-bicyclo[4.3.1]dec-3-yl acetate (see example 3) by saponification and subsequent etherification.

Their analytical characteristics were as follows:
endo methyl ether:
IR (neat): 3080, 2920, 2800, 1640, 1450, 1100, 880 cm$^-$
$^1$H-NMR (360 MHz): 0.87 (s, 3H); 0.92 (s, 3H); 1.0–2.03 (m, 12H); 2.53 (m, 1H); 3.27 (s, 3H); 4.6 (d, J=3 Hz, 1H); 4.71 (d, J=3 Hz, 1H, ) δppm $^{13}$C-NMR (90 MHz): 25.9 (t); 28.1 (t); 29.1 (q); 30.2 (q); 34.2 (t); 34.3 (t); 34.5 (s); 37.3 (d); 41.2 (t); 52.6 (d); 55.9 (q); 77.4 (d); 110.5 (t); 153.2 (s) δppm MS m/z 208 (M$^+$, 0); 19 (5); 176 (7); 165 (3); 161 (17); 147 (8); 137 (26); 121 (69); 111 (63); 107 (44); 91 (47); 85 (100); 79 (63); 67 (21); 41 (38).

exo methyl ether:
IR (neat): 3080, 2920, 2800, 1640, 1450, 1100, 880 cm$^{-1}$
$^1$H-NMR (360 MHz): 0.85 (s, 3H); 0.91 (s, 3H); 1.06 (m, 1H); 1.36–1.92 (m, 9H); 2.09 (dd, J=3, 10 Hz, 1H); 2.61 (m, 1H); 3.31 (s, 3H); 4.61 (d, J=3 Hz, 1H ); 4.83 (d, J=3 Hz, 1H, ) δppm $^{13}$C-NMR (90 MHz): 24.2 (t); 27.2 (q); 27.9 (q); 28.3 (t); 31.0 (t); 31.3 (t); 31.2 (s); 36.7 (d); 41.2 (t); 51.5 (d); 55.9 (q); 82.3 (d); 111.9 (t); 151.3 (s) δppm MS m/z 208 (M$^+$, 5); 193 (1); 176 (15); 161 (39); 152 (20); 147 (13); 137 (24); 133 (41); 120 (100); 107 (79); 91 (72); 85 (34); 79 (100); 71 (33); 67 (24); 55 (27); 41 (51).

Odor: described in the specification b) 3-ethoxy-7,7-dimethyl-10-methylene-bicyclo[4.3.1]decane The ethyl ethers were prepared according to the process described above, by using ethyl bromide as halide. After bulb-to-bulb-distillation at 150° and 10 Pa, 0.95 g of a colorless oil were obtained.
Yield=89% of theoretical yield
Mixture composed of 2 isomers (71/29).
endo ethyl ether (peak 1; 29% of the mixture).
exo ethyl ether (peak 2; 71% in the mixture).
Odor: intense, woody-cedar with a note of grilled peanuts and a base note reminiscent of rhubarb and grapefruit.

IR (neat): 3080, 2940, 2800, 1640, 1460, 1100, 890 cm$^{-1}$
$^1$H-NMR (360 MHz): 0.84 (s, 3H, exo); 0.86 (s, 3H, endo); 0.89 (s, 3H, exo); 0.91 (s, 3H, endo); 1.05 (large s, 1H); 1.15 (t, J=7H, 3H, exo);1.17 (t, J=7H, 3H, endo); 1.31–2.01 (m, 10H); 2.1 (large s, 1H); 2.6 (m, 1H, exo); 2.68 (m, 1H, endo); 3.30–3.50 (m, 2H); 4.59 (d, J=3 Hz, 1H, endo); 4.62 (d, J=3 Hz, 1H, exo); 4.82 (d, J=3 Hz, 1H, exo); 4.89 (d, J=3 Hz, 1H, endo) δppm $^{13}$C-NMR (90 MHz) 15.8 (q); 24.5 (t); 26.1 (t, endo); 27.2 (q); 28.1 (t); 28.5 (q); 31 (t); 34.2 (s); 35.1 (t); 36.7 (d); 37.4 (d, endo); 42.4 (t); 51.4 (d); 52.6 (d, endo); 63.3 (t); 63.5 (t, endo); 80.7 (d); 110.4 (t, endo); 111.9 (t); 151.4 (s); 153 (s, endo) δppm MS m/z 222 (M$^+$, 1); 207 (1); 176 (9); 161 (30); 147 (11); 133 (36); 120 (44); 107 (69); 99 (26); 91 (73); 85 (39); 79 (100); 67 (28); 55 (38); 41 (47).

Example 3
Preparation of the Esters of Formula (IIa")
7,7-dimethyl-10-methylene-bicyclo[4.3.1]dec-3-yl acetate In a 3-necked flask which was equipped with a reflux condenser, there were placed, under $N_2$-atmosphere, 0.9 g (4.6 mmoles) of 7,7-dimethyl-10-methylene-bicyclo[4.3.1]decan-3-ol, 8 ml of acetic anhydride and 1 drop of phosphoric acid. The reaction mixture was stirred overnight at room temperature. Then 50 ml of $H_2O$ were added and the solution stirred one more night at room temperature. The resulting mixture was taken up in ether, washed to neutrality with brine and dried over $Na_2SO_4$. After filtration and concentration in vacuo, the product was distilled in a bulb-to-bulb apparatus at 150° C. (10 Pa). There were obtained 1.09 g of a colorless oil in 99% of the theoretical yield. The thus-obtained mixture was composed of 2 isomers (71/29) which were separated by gas chromatography on a chemically inert CARBOWAX® column having a length of 5 meters.

Odor: described in the specification
exo acetate (peak 1; 71% of the mixture).
IR (neat) 3060, 2950, 1750, 1640, 1460, 1370, 1250, 1040, 900 cm$^{-1}$
$^1$H-NMR (360 MHz) 0.85 (s, 3H); 0.9 (s, 3H); 1.08 (dd, J=5, 14 Hz, 1H); 1.4 (dd, J=4, 14 Hz, 1H); 1.5–1.9 (m, 8H); 2.0 (s, 3H); 2.1 (m, 1H); 2.62 (m, 1H); 4.64 (d, J=3 Hz, 1H); 4.84 (d, J=3 Hz, 1H); 4.89 (m, 1H) δppm $^{13}$C-NMR (90 MHz): 21.6 (q); 23.9 (t); 27.3 (q); 28 (q); 28 (t); 30.8 (t); 32 (t); 34.3 (s); 36.8 (d); 40.8 (t); 51.4 (d); 75.6 (t); 112.4 (t); 151 (s); 170.5 (s) δppm MS m/z 236 (M$^+$, 0); 176 (56); 161 (47); 147 (13); 133 (48); 120 (83); 105 (93); 91 (100); 79 (82); 69 (41); 55 (31); 43 (83).

endo acetate (peak 2; 29% of the mixture)
IR (neat): 3060, 2950, 1750, 1640, 1460, 1370, 1250, 1040, 900 cm$^{-1}$
$^1$H-NMR (360 MHz) 0.87 (s, 3H); 0.91 (s, 3H); 1.08 (d, J=14 Hz, 1H); 1.39 (d, J=14 Hz, 1H); 1.45–2.07 (m, 9H); 1.99 (s, 3H); 2.58 (m, 1H); 4.64 (d, J=3 Hz, 1H); 4.78 (d, J=3 Hz, 1H); 4.86 (m, 1H) δppm $^{13}$C-NMR (90 MHz): 21.6 (q); 25.7 (t); 28.3 (q); 28.3 (q); 29 (t); 30 (t); 31.9 (t); 34.5 (s); 34.5 (t); 36.9 (d); 52.5 (d); 72.5 (d); 111.6 (t); 151.8 (s); 170 (s) δppm MS m/z 236 (M⁺, 0); 194 (5); 176 (20); 161 (40); 147 (23); 136 (48); 120 (65); 107 (90); 91 (89); 79 (84); 69 (40); 55 (36); 43 (100).

Example 4

Perfuming Composition

A base perfuming composition for a perfume of the masculine type was prepared from the following ingredients:

| Ingredients | Parts by weight |
| --- | --- |
| Linalyl acetate | 350 |
| 10%* Ambrinol[1] | 20 |
| AMBROX ®[2] | 30 |
| Lemon oil | 600 |
| Coumarin | 60 |
| 10%* α-Damascone[3] | 50 |
| Dihydromyrcenol[4] | 660 |
| Estragon oil | 20 |
| 10%* FARENAL ®[5] | 35 |
| 2-Methyl-4-(2,2,3-trimethyl-3-cyclopenten-1-yl)-4-penten-1-ol[6] | 5 |
| GALAXOLIDE ® 50[7] | 200 |
| Geraniol | 40 |
| Geranium essential oil (China) | 120 |
| HEDIONE ®[8] | 350 |
| Laurel oil | 10 |
| Linalol | 150 |
| LYRAL ®[9] | 80 |
| 10%* 1-(2,6,6-Trimethyl-1-cyclohexyl)-3-hexanol[10] | 70 |
| OSYROL ®[11] | 130 |
| TONALIDE ®[12] | 500 |
| Vanillin | 20 |
| Total | 3500 |

*in dipropylene glycol
[1] octahydro-2,5,5-trimethyl-2-naphthalenol; origin: Firmenich SA, Geneva, Switzerland
[2] 8,12-epoxy-13,14,15,16-tetranorlabdane; origin: Firmenich SA, Geneva, Switzerland
[3] origin: Firmenich SA, Geneva, Switzerland
[4] 2,6-dimethyl-7-octen-2-ol; origin: International Flavors and Fragrances Inc., U.S.A.
[5] 2,6,10-trimethyl-9-undecanal; origin: Haarmann & Reimer GmbH, Germany
[6] origin: Firmenich SA, Geneva, Switzerland
[7] 1,3,4,6,7,8-hexahydro-4,6,6,7,8,8-hexamethyl-cyclopenta[g]-2-benzopyrane; origin: International Flavors and Fragrances Inc., U.S.A.
[8] methyl dihydrojasmonate; origin: Firmenich SA, Geneva, Switzerland
[9] 4-(4-hydroxy-4-methylpentyl)-3-cyclohexene-1-carbaldehyde and 3-(4-hydroxy-4-methylpentyl)-3-cyclohexene-1-carbaldehyde; origin: International Flavors & Fragrances Inc., U.S.A.
[10] origin : Firmenich SA, Geneva, Switzerland
[11] 7-methoxy-3,7-dimethyl-2-octanol; origin: Bush, Boak Allen Ltd., Great-Britain
[12] 7-acetyl-1,1,3,4,4,6-hexamethyltetraline; origin: PFW, Naarden, Netherlands To this base composition of the citrus, woody, musky type, there were added 1700 parts by weight of 3-methoxy-7,7-dimethyl-10-methylene-bicyclo[4.3.1]decane. There was thus obtained a new composition in which the woody note had acquired the typical freshness of the classical eau de cologne, showing a much appreciated citrus character. When there were added 1700 parts by weight of 7,7-dimethyl-10-methylene-bicyclo[4.3.1]dec-3-yl acetate, there was obtained a new composition which, in addition to its woody base note, showed a nice rooty connotation reminiscent of vetyver.

Example 5

Perfuming Composition

A base perfuming composition for a cologne of the masculine type was prepared from the following ingredients.

| Ingredients | Parts by weight |
| --- | --- |
| Benzyl acetate | 60 |
| Linalyl acetate | 450 |
| Phenylethyl acetate | 5 |
| 50%* Cinnamic alcohol | 30 |
| Amylcinnamic aldehyde | 100 |
| 10%* C-10 Aldehyde | 40 |
| 1%* 4-(4-Hydroxy-1-phenyl)-2-butanone[1] | 30 |
| Bergamot oil | 600 |
| Caraway oil | 70 |
| 10%** AMBROX ®[2] | 30 |
| Citral pure | 320 |
| Allyl phenoxyacetate[3] | 50 |
| Coumarin | 65 |
| Eugenol | 90 |
| Geranium essential oil (China) | 90 |
| HEDIONE ®[4] | 200 |
| Heliopropanal[5] | 40 |
| 10%*** Indol | 70 |
| IRALIA ®[6] | 80 |
| Jasmone | 5 |
| Lavender oil | 480 |
| Linalol | 800 |
| Mandarine oil | 100 |
| Oak moss abs. (Morocco) | 60 |
| Patchouli oil | 150 |
| Petitgrain oil | 40 |
| Rosemary oil | 30 |
| Undecalactone | 5 |
| β-Ionone[7] | 10 |
| Total | 4100 |

*in dipropylene glycol
**in 2-(2-ethoxyethoxy)-1-ethanol; origin: Firmenich SA Geneva, Switzerland
***in triethanolamine
[1] origin: Firmenich SA, Geneva, Switzerland
[2] see example 4
[3] origin: Firmenich SA, Geneva, Switzerland
[4] see example 4
[5] 3-(1,3-benzodioxol-5-yl)-2-methylpropanal; origin: Firmenich SA, Geneva, Switzerland
[6] methylionone; origin: Firmenich SA, Geneva, Switzerland
[7] origin: Firmenich SA, Geneva, Switzerland To this base composition, there were added 150 parts by weight of 3-methoxy-7,7-dimethyl-10-methylene-bicyclo[4.3.1]decane. There was thus observed that the woody base note was intensified, as was the citrus character already present in this base composition, the latter effect being even more pronounced. The addition of 150 parts by weight of 7,7-dimethyl-10-methylene-bicyclo[4.3.1]dec-3-yl acetate conferred more volume to the composition and intensified the woody base note of the base composition, while imparting an effect of the chypre type to the composition, which resulted from the accord of the compound of the invention with the oak moss.

Example 6

Perfuming Composition

A base perfuming composition intended for the preparation of a masculin cologne of the "wood-fougère" type was prepared from the following ingredients:

| Ingredients | Parts by weight |
| --- | --- |
| Linalyl acetate | 500 |
| Bergamot essential oil | 200 |
| Citral pure | 20 |
| Lemon oil | 60 |
| Citronellol | 90 |

-continued

| Ingredients | Parts by weight |
|---|---|
| 50%* Civette (purif.) | 20 |
| Coranol[1] | 50 |
| Coumarin | 80 |
| 2-Methyl-4-(2,2,3-trimethyl-3-cyclopenten-1-yl)-4-penten-1-ol[2] | 30 |
| Geranium essential oil (China) | 30 |
| HEDIONE ®[3] | 400 |
| Lavandin oil | 180 |
| LYRAL ®[4] | 300 |
| Mandarine oil | 60 |
| 50%* Oak moss abs. (Morocco) | 40 |
| Patchouli oil | 720 |
| Vanillin | 20 |
| Total | 2800 |

*in dipropylene glycol
[1] 4-cyclohexyl-2-methyl-2-butanol; origin: Firmenich SA, Geneva, Switzerland
[2], [3], [4] see example 4

To this base composition, there were added 400 parts by weight of 3-methoxy-7,7-dimethyl-10-methylene-bicyclo[4.3.1]decane to obtain a new composition in which the woody note had become fresher and had acquired more volume.

When there were added to this base, which already showed a clear woody note, 400 parts by weight of 7,7-dimethyl-10-methylene-bicyclo[4.3.1]dec-3-yl acetate, there was conferred to it a more rooty, vetyver dimension.

Example 7
Perfuming Composition

A perfuming composition for an oriental type cologne was prepared, with the following ingredients.

| Ingredients | Parts by weight |
|---|---|
| Benzyl acetate | 130 |
| Linalyl acetate | 230 |
| 10%* Ambrinol[1] | 30 |
| Astrotone[2] | 300 |
| 1%* 4-(4-Hydroxy-1-phenyl)-2-butanone[3] | 20 |
| 10%** AMBROX ®[4] | 80 |
| 10%* γ-Decalactone[5] | 90 |
| 2-Methyl-4-(2,2,3-trimethyl-3-cyclopenten-1-yl)-4-penten-1-ol[6] | 20 |
| GALAXOLIDE ® 50[7] | 700 |
| Geranium essential oil (Africa) | 30 |
| HEDIONE ®[7] | 930 |
| Linalol | 125 |
| LYRAL ®[8] | 310 |
| δ-Nonalactone[9] | 10 |
| Patchouli oil | 20 |
| Vanillin | 635 |
| VERTOFIX COEUR ®[10] | 340 |
| Total | 4000 |

*in dipropylene glycol

**in 2-(2-ethoxyethoxy)-1-ethanol; origin: Firmenich SA, Geneva, Switzerland
[1], [4], [6], [7], [8] see example 4
[2] 1,4-dioxa-5,17-cycloheptadecanedione; origin: Firmenich SA, Geneva, Switzerland
[3] see example 5
[5] origin: Firmenich SA, Geneva, Switzerland
[9] origin: Firmenich SA, Geneva, Switzerland
[10] mixture of 9-acetyl-8-cedrene and cedar sesquiterpenes; origin: International Flavors and Fragrances Inc., U.S.A.

When there were added to this base composition 400 parts by weight of 3-methoxy-7,7-dimethyl-10-methylene-bicyclo[4.3.1]decane, there was conferred to it an excellent citrus character, with the effect of the compound of the present invention being very marked, as is generally the case when this compound is used in high concentrations.

The same amount of 7,7-dimethyl-10-methylene-bicyclo[4.3.1]dec-3-yl acetate adds to this base composition a natural woody-classical effect due to its marriage with the patchouli.

What is claimed is:

1. A compound of formula

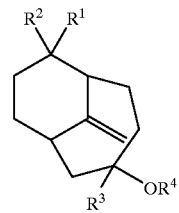

(II)

in which

R$^1$ and R$^2$ are identical or different and represent each a methyl or ethyl group, R$^3$ represents hydrogen or an alkyl group from C$_1$ to C$_4$, linear or branched, R$^4$ represents hydrogen, an alkyl group from C$_1$ to C$_4$, linear to branched, or an acyl group of formula R$^5$C(O)—, R$^5$ being hydrogen or an alkyl group from C$_1$ to C$_4$, linear or branched.

2. 3-Methoxy-7,7-dimethyl-10-methylene-bicyclo[4.3.1]decane or 7,7-dimethyl-10-methylene-bicyclo[4.3.1]dec-3-yl acetate.

3. Exo-3-methoxy-7,7-dimethyl-10-methylene-bicyclo[4.3.1]decane, endo-3-methoxy-7,7-dimethyl-10-methylene-bicyclo[4.3.1]decane, exo-7,7-dimethyl-10-methylene-bicyclo[4.3.1] dec-3-yl acetate or endo-7,7-dimethyl-10-methylene-bicyclo[4.3.1]dec-3-yl acetate.

* * * * *